US005753477A

United States Patent [19]
Chan

[11] Patent Number: 5,753,477
[45] Date of Patent: May 19, 1998

[54] MAGNETO-BIOLISTIC METHODS

[75] Inventor: Daniel C.F. Chan, Denver, Colo.

[73] Assignee: University Technology Corporation, Boulder, Colo.

[21] Appl. No.: 617,685

[22] Filed: Mar. 19, 1996

[51] Int. Cl.$^6$ .................................................. C12N 15/63
[52] U.S. Cl. .................................. 435/172.3; 435/320.1;
435/172.1; 435/252.3; 435/252.33; 435/325;
435/348; 435/351; 435/352; 435/410; 435/419;
435/420; 435/431; 800/2; 800/205; 800/220;
800/230; 800/250; 800/DIG. 1; 935/52;
935/53; 935/54; 935/55
[58] Field of Search ....................... 435/320.1, 172.3,
435/172.1, 252.3, 252.33, 325, 348, 349,
351, 352, 410–431; 514/44; 935/52, 53,
54, 55, 56, 57; 800/2, 205, 220, 230, 250

[56] References Cited

U.S. PATENT DOCUMENTS

| 4,452,773 | 6/1984 | Molday | 424/1.1 |
|---|---|---|---|
| 4,945,050 | 7/1990 | Sanford et al. | 435/172.3 |
| 4,971,910 | 11/1990 | Zimmerman | 435/285.1 |
| 5,015,580 | 5/1991 | Cristou et al. | 435/172.3 |
| 5,149,655 | 9/1992 | McCabe et al. | 604/57 |
| 5,411,730 | 5/1995 | Kirpotin | 424/93.22 |
| 5,498,421 | 3/1996 | Grinstaff et al. | 424/450 |
| 5,516,670 | 5/1996 | Kuehnle et al. | 435/172.3 |
| 5,585,479 | 12/1996 | Hoke et al. | 536/24.5 |

OTHER PUBLICATIONS

White (1972) in: Modern College Physics, sixth edition, D. Van Nostrand Company, New York, NY, p. 404).

Stein (Ed. in Chief) 1993 in: Internal Medicine, 4th edition, Mosby Year Book, pp. 699–715.

Rennie et al. (eds) 1996 Scientific American 275(3): 126–132.

Orkin et al. (7 Dec. 1995) "Report And Recommendations Fo The Panel To Assess The NIH Investment In Research On Gene Therapy".

Widder et al., Proc. Soc. Exp. Bio. & Med. 58: 141–146 (1978).

Belehradek et al. Biochem. Biophys. Acta. 1190: 155–163 (1994).

Sanford et al. Methods in Enzymology 217: 483–509 (1993).

T.M. Klein et al., Bio/Technology 10:286–291 (1992).

N.S. Yang, 1992 CRC Crit. Rev. Biotechnol. 12 pages 335–356.

Casas et al., Proc. Natl Acad. Sci. 90: 11212–11216 (1993).

Woffendin et al., Proc. Batl Acad. Sci. 91: 11581 11585 (1994).

Fitzpatrick–McElligott, Bio/Tech. 10: 1036–1040 (1992).

Ellis et al. Bio/Tech 11: 84–89 (1993).

Jiao et al. Bio/Tech 497 (1993) 11: 497–502 (1993).

Primary Examiner—Christopher S.F. Low
Attorney, Agent, or Firm—Macheledt Bales & Johnson, LLP; Kristine H. Johnson

[57] ABSTRACT

The present invention discloses methods to transfect cells, comprising applying a strong magnetic field in pulses so as to affect a plurality of substance-carrying magnetic microparticles, the complexes being in physical proximity to a plurality of cells such that when the magnetic field is applied, the magnetic microparticles are pulled into the nuclei and/or cytoplasm of the cells.

28 Claims, No Drawings

MAGNETO-BIOLISTIC METHODS

This application hereby incorporates by reference the following issued U.S. Patent: U.S. Pat. No. 5,411,730, issued on May 17, 1995.

BACKGROUND OF THE INVENTION

In the past decade, a new means for delivering substances into cells has emerged. Researchers have successfully bombarded cells with high-velocity microparticles and carried substances into the cells on the surface of the microparticles. In *Particle Bombardment Technology for Gene Transfer*, (1994) edited by Ning-Sun Yang and Paul Cristou, the new field is described in great detail.

Yang and Cristou not only describe the history and principles behind particle bombardment technology, but they describe the applications as well. Although their description is limited to apparatuses which use accelerating forces supplied by gunpowder detonation, high voltage electric discharge through a water droplet or gas pulse, (Yang, at 6), their description of applications for substance delivery into cells is informative background to the present invention. The applications of particle bombardment technology, as described by Yang and Cristou, include agricultural improvements, evolution studies, molecular biology research, gene therapy and genetic immunization. Yang, at Chapters 3–7. Yang and Cristou also provide parameters for target tissue preparation, microparticle/substance complex preparation, and DNA construct preparation. Yang, at 10–29.

Other previous substance delivery methods have included the use of magnetic nicrospheres to deliver substances into cells. For example, Widder et al. have described the development of a magnetically responsive biodegradable magnetic drug carrier with the capacity to localize both carrier and chemotherapeutic agent by magnetic means to a specific in vivo target site after systemic administration. Widder et al., 58 *Proc. Soc. Exp. Bio. & Med.* 141 (1978). The carrier consists of albumin microspheres 0.2–2 microns in diameter containing both magnetic $Fe_3O_4$ microparticles (10–20 nm in diameter) and a chemotherapeutic agent entrapped in the albumin matrix. This complex can be held in the desired location via an external static permanent magnet. It has been reported that these complexes are internalized by tumor cells in vitro and in vivo following intra-peritoneal (ip) injection, possibly through passive phagocytosis process. However, controlled localization of drug carriers including this type of magnetic microspheres or conventional liposomes has been difficult to achieve. Despite efforts to impart specificity by modifying surface charge, varying vesicle size and varying lipid components, intravascular administration of such carriers results in their uptake predominately by the reticuloendothelial system. Efforts to improve the targetability of magnetic microparticles and, at the same time, to reduce phagocytosis by the reticuloendothelial system using immuno-conjugated stealth-like liposomal magnetic microparticles have been described in U.S. Pat. No. 5,411,730.

Another known method for substance delivery into cells is the use of an electric pulse to facilitate the delivery of drugs. In 1190 *Biochem. Biophys. Acta.* 155 (1994), Belehradek et al. describe that certain charged compounds can be delivered better if pulsed with electricity after administration. The drawbacks of this method are the use of very high voltage applied via the electrodes, which may cause undesirable effects in some patients, and only a limited number of small charged compounds can be used with this approach.

In Zimmerman, U.S. patent application Ser. No. 4,971,910 (1990), there is described a process for fusing cells together using a nonhomogeneous magnetic field. The cells are doped with magnetic particles and brought into contact with each other with an external magnet, and then an electric pulse is given to merge the membranes. It is not described in the patent how the cells are doped with magnetic particles. However, electroporation has been commonly used to introduce some charged macromolecules into cells in in vitro experiments.

One practical application for many biolistic substance delivery methods is gene therapy. Gene therapy will have a major impact on human health in the next century and has great potential for the treatment of a wide spectrum of genetic, neoplastic, and infectious diseases. W. F. Anderson, 256 *Science* 808 (1992). Two main experimental strategies for gene therapy are currently being explored. One approach is in vivo gene transfer into targeted somatic tissues; the other approach utilizes ex vivo gene transfer into tissue or cell explants or primary culture, which are then transplanted into host animals. Despite the existence of many transformation techniques, specifically targeted gene delivery remains a field in need of improvement. J. A. Wolff, *Gene Therapeutics* (1994).

Particle bombardment has been shown to be effective under various experimental conditions with in vivo, ex vivo, and in vitro mammalian gene transfer systems. Sanford et al, 217 *Methods in Enzymology* 483 (1993) and T.M. Klein et. al., 10 *Bio/Technology* 286 (1992). Russell's technique involves accelerating DNA-coated microprojectiles directly into cells or tissues, driven by a high pressure gas shock procedure. The gas shock can be generated by several mechanisms, namely: chemical explosion (gun powder), electric explosion of a water droplet, or a discharge of compressed air or helium. ibid.

Researchers elaborating on Russell's work commonly use gold or tungsten particles of 0.6 to 2.5 μm in diameter as the microprojectile. Russell's approach has been successfully used to deliver active genes into many plant cells and in mammalian cells. Cristou et al., U.S. patent application Ser. No. 5,015,580 (1991). More recently, several reports have demonstrated particle bombardment's utility in transfection of freshly isolated tissue explants samples, including tissue slices, tissue clumps, and cell aggregates, providing a new approach for gene transfer into surgically derived tissue samples. N. S. Yang, 12 *CRC Crit. Rev. Biotechnol.* 335 (1992).

In U.S. patent application Ser. No. 4,945,050, Sanford et al. disclose three apparatuses for propelling small particles into cells. The first utilizes a blast of gas to propel particles, the second utilizes an explosive, and the third utilizes release of electrostatic interaction of the particles from a high-velocity rotating drum.

The biolistic process using gas shock approach was commercially developed by Dupont and a commercial model is now available through Bio-Rad. Its usefulness in gene delivery is evidenced by the increasing number of publications on its application in the literature. Klein et al., 10 *Bio/Technology* 286 (1992), Fitzpatrick-McElligott, 10 *Bio/Technology* 1036 (1992), Jiao et al., 11 *Bio/Technology* 497 (1993), Ellis et al., 11 *Bio/Technology* 84 (1993), Casas et al., 90 *Proc. Nat. Acad. Sci.* 11212 (1993), Woffendin et al., 91 *Proc. Nat. Acad. Sci.* 11581 (1994). A hand-held device for introducing particles into cells via electric impulse is disclosed in McCabe et al., U.S. Pat. No. 5,149,655 (1992).

Any methods that improve the delivery of genes into target cells will be of great value to the molecular biologists in the fast growing field of genetic engineering. Moreover, with the momentum generated by the Human Genome Project, gene therapy is maturing very fast and will have a major impact on human health in the very near future.

SUMMARY OF THE INVENTION

The methods of the present invention utilize superparamagnetic and/or ferromagnetic microparticles to carry substances into cells via a pulsed magnetic field. The present methods differ from the previously-described methods in that the microparticles are not propelled from a distance by a violent force. The present invention provides a safer and more controlled method for introducing substances into tissues. Moreover, one aspect of the present invention utilizes super-paramagnetic particles which do not retain their magnetic properties in the absence of a magnetic field; therefore, the particles will not aggregate in the cell after penetration. Lastly, the small size of the particles used and the mode of driving force used results in less trauma to the cells and improved transfection frequency.

It is therefore an object to provide methods for introducing substance-carrying magnetic materials into cells via pulsed magnetic forces.

It is yet another object to provide methods for treating cancer cells using magnetic materials and pulsed magnetic forces.

It is yet another object to provide methods to treat genetic diseases using magnetic materials and pulsed magnetic forces.

It is yet another object to provide methods for molecular biology research using magnetic materials and pulsed magnetic forces.

It is yet another object to provide methods for genetic immunization using magnetic materials and pulsed magnetic forces.

It is yet another object to provide methods for agricultural improvements using magnetic materials and pulsed magnetic forces.

Other objects and features of the present invention will be apparent from the following detailed description of the preferred embodiment.

DEFINITIONS

When used in the present application, the following terms shall have the following meanings:

Adherent: any substance or mechanism by which substances, including, but not limited to, DNA, RNA, proteins, chemotherapeutic agents, to be carried inside the targeted cells by magnetic microparticles. It can mean a coating on the particle, such as, but not limited to, biopolymers, proteins, or charged lipids.

Nucleic Acids: sense or antisense nucleic acids, including DNA, RNA (ie. mRNA, tRNA, rRNA and those which function as ribozymes) and oligonucleotides.

PRINCIPLE OF THE METHODS

In the absence of an applied magnetic field, superparamagnetic microparticles of size 10 to 100 nm in diameters undergo Brownian motion. When an external magnetic field of moderate strength of 100 to 200 gauss is applied, these particles become magnetized and form into small magneto-needles because of its high initial magnetic susceptibility (0.1 to 0.7 emu/gm Fe/Gauss) and relatively low saturation magnetization (80 emu/gm Fe). In the continual presence of applied field, the small needles can undergo needle-needle interactions and coalesce into bigger needles. These needles generally move past one another until their ends join to each other. Moreover, these needles continue to move slowly toward the applied pole surface of the external magnet. When a stronger magnetic field is applied, the needles move much faster toward the applied magnet. In general, because of the short duration (micro- to milli-seconds) of a pulse in a high magnetic field (2 to 50 Teslas), two stages of magnetic induction are required to act on the particles in order for the particles to accelerate to a high enough velocity to penetrate a single cell membrane or multi-cell layers.

First, the superparamagnetic or ferromagnetic microparticles are pre-magnetized with a primary solenoid of 100 to 1000 Gauss briefly for 1 to 10 seconds (although pre-magnetization is not essential for ferromagnetic particles, so long as they are already magnetic) and immediately followed by the secondary high magnetic pulse (2 to 50 Teslas) of 10 to 200 milliseconds produced by a second solenoid, which serves to accelerate the pre-magnetized particles into the target. Also disclosed is a method as above wherein the pulse(s) is 1 microsecond to 200 milliseconds in length. The target and the magnetic microparticles are placed along the Z-axis and at a position of maximum field gradient directly outside of the secondary pulse coil. Since a homogeneous field is not required for the magnetic biolistic process, any coil which produces high field gradients described will function in the present method. Depending on the cell types, ie. single cell or multi-cell layers, single and/or multi-pulses can be applied to the microparticles and the target. In the absence of a high pulsed field device (field strength greater than 2 Teslas), a coil capable of delivering multi-pulses of continuously moderate field strength (0.5 to 2 Teslas) with pulse durations of 10 to 200 milliseconds, can also be used to deliver superparamagnetic and/or ferromagnetic microparticles into a single cell layer. Intervals between pulses should be kept as close as possible. This set up is more suitable for in vitro single cell layer transfection.

DETAILED DESCRIPTION OF THE METHODS

The present invention establishes an improved method of substance delivery into a variety of cell types using superparamagnetic and ferromagnetic microparticles under the influence of pulsed magnetic field. The improved method can be utilized to treat a variety of disease states.

In general, the method for delivering a substance or substances into a cell involves using superparamagnetic and/or ferromagnetic microparticles which are acted upon by a pulsed magnetic field. Often, prior to use in the present method, the microparticles are coated with biodegradable biopolymers or lipids. The lipids can carry positive or negative charges, and also a substance or substances, preferably carrying charges opposite to that of the coating, which, thereby, is complexed to the microparticle. In practicing the present invention, a microparticle, coated or not coated, is pulled into the cell using a single strong magnetic pulse or multi-pulses of moderate field strengths. In general, the superparamagnetic and/or ferromagnetic particles will be pre-magnetized with a weak DC solenoid coil of about 200 gauss for a few seconds prior to the immediate generation of the pulsed high magnetic field. This second magnetic impulse serves as the primary attractive force to accelerate or drag the magnetized particles into the target. Thus, cells or tissues in the path of the magnetic microparticles will become the bombarded target as soon as the second strong magnetic pulse is triggered. By correctly positioning the magnetic pole, ie. at the position of maximum field gradient, it is possible to accelerate the magnetic microparticels to a velocity fast enough for the particles to penetrate through the plasma membrane of the cells. In general, because of the viscous surroundings, a pulse field of at least 2 to 50 Teslas is required to accelerate the microparticles to the required velocity. However, a continuous multi-pulses of moderate field strength of at least 0.5 to 2 Teslas may work as well. Particle location after pulse can be determined in a number of ways. Often, but not always, it is desirable to achieve maximum particle penetration with minimal cell death.

The present invention is more easily understood when the starting materials, the method parameters, and the practical applications of the methods themselves are understood. Therefore, these aspects of the invention will be discussed individually. However, the present invention is, like all inventions, more than the sum of its parts.

STARTING MATERIALS
The Superparamagnetic Microparticles

The present inventor has been actively involved in developing novel superparamagnetic iron oxides with unusually high magnetic susceptibility and high saturation magnetization for therapeutic and diagnostic applications in medicine. He, along with others, has obtained a patent for the development of these superparamagnetic iron oxides. That patent, U.S. Pat. No. 5,411,730, issued on May 17, 1995, has been incorporated by reference into this patent application. Any of the microparticles mentioned in that patent would be useful in the present invention, whether for use in medical applications or not. The size (50 to 200 nm) and physical characteristics (particularly the density and magnetic properties) of these microparticles makes them ideal for cell penetration. The microparticles may be manufactured according to the specifications in the issued patent. However, ferromagnetic microparticles, preferrably of a size less than 500 nm are also useful.

A variety of ferromagnetic microparticulated materials have been reported for the use in ferromagnetic hyperthermia (referenced in the patent incorporated by reference) and several dextran-coated superparamagnetic iron oxides have been used in applications such as contrast agents for magnetic resonance imaging in diagnostic medicine. Pouliquen, et al. 9 *J. Mag. Res. Imaging* 275 (1991) and Fahlvik, et al., 3 *J. Mag. Res. Imaging* 187 (1989); magnetic labeling and sorting of cells, Owen, 16 *J. Immunogenetics* 117 (1989); and bone marrow purging for treatment of cancer patients Bieva, et al. 178 *Exp. Hematop.* 914 (1989). These types of microparticles have been shown to produce little, if any toxicity to animals, including humans. Bacon, et al., 110 *J. Lab. Clin. Med.* 164 (1987) and Weissleder, et al., 152 *Am. J. Radiology* 167 (1989).

Often, it is desirable to coat a microparticle designed for use in a living system with an biologically inert material such as dextran or other polysaccharides. When a microparticle is coated with dextran, for example, the iron oxides are non-toxic, non-carcinogenic and biodegradable. Dextran-coated microparticles have been used safely as a contrast agent in magnetic resonance imaging. Pouliquen, et al. 9 *J. Mag. Res. Imaging* 275 (1991) and Ferrucci, et al., 9 *J. Mag. Res. Imaging* 943 (1991).

The Adherents

If the microparticle will be carrying a substance into the cell, the substance must somehow be physically associated with the microparticle, so as to prevent it from being left on the outside of the cell when the microparticle penetrates the cell wall and/or membrane. In this case, a binding agent can be utilized.

When determining which adherent to chose, it is important to take into consideration the physical properties of the substance chosen. For instance, if a negatively-charged substance were chosen, it would be desirable to chose a positively-charged adherent. Those in the art are familiar with the chemical interactions which would provide adequate binding properties.

For instance, the microparticles used in the present invention can be easily coated with various cationic lipid formulations which themselves can provide a good binding surface for multiple DNA molecules. The cationic lipid formulations also allow the excessive positively charged lipids to interact with the negative charged biological surface of the targeted cells.

Several different cationic lipid formulations or cationic amphiphiles, such as DOTMA (dioleyloxypropyl trimethyl ammonium chloride), DOTAP (dioleoyl diacyl trimethyl ammonium propane), DDAB (dimethyl dioctadecyl ammonium bromide), and many others can be obtained from several different commercial sources including BRL, Avanti Polar Lipids, and Sigma Biochemicals and many others.

These cationic lipids, either alone or mixed with DOPE (dioleoyl phosphatidyl ethanolamine), can be easily coated on the magnetic microparticles. Briefly, cationic lipids can be dissolved in an organic solvent, and to that solution an appropriate amount of magnetic microparticles (ie. bare iron oxide) in ethanol can be added. The mixture can then be vortexed and sonicated, and the solvent removed by rotary vacuum evaporation. The mixture should not be over-dried, otherwise it will be difficult to rehydrate in the next step. Water can be added to the residual deposit and the resulting mixture vortexed and sonicated on ice until a slurry colloidal solution is obtained. Large aggregates can be removed by low speed centrifugation.

If the microparticle is coated with dextran, for example, the dextran coating can be chemically modified and conjugated with other proteins or polyamines such as poly-L-lysine, polyarginine or other biopolymers with positive charges. These chemical modifications allow for binding of nucleic acids through ionic interaction. A special phospholipid derivative, polyethyleneglycol-conjugated distearoyl phosphatidylethanolamine (PEG-DSPE) can also be introduced into cationic magneto-liposomes to improve the circulation lifetimes of the complex, as described in U.S. Pat. No. 5,411,730. Furthermore, specific monoclonal antibodies can also be conjugated with PEG-DSPE with appropriate linkers and added to the cationic PEG-magneto-liposomes to increase targetability of the complex.

If agents other than nucleic acids are to be carried on the magnetic microparticles, the particles can be coated with biopolymers carrying positive or negative charges. Pharmaceuticals carrying charges opposite to the coatings can be complexed onto the particles through ionic interaction. These complexes can also be delivered into cells or tissues with the herein described magneto-biolistic process.

The Substances Carried by the Microparticles

Depending on the particular coating, a number of substances can be carried via the magnetic microparticles. For example, nucleic acids, including plasmids, genetic constructs, ribozymes, viruses, or proteins can be complexed onto magnetic microparticles which have been coated with positively-charged biopolymers or cationic lipids. As another example, pharmaceutical compounds carrying positive or negative charges can also form transient complexes with microparticles which have been coated with biopolymers (ie. chondroitin sulphate or chitosan) which carry charges opposite to the compound(s) carried. Likewise, nucleic acids, proteins peptides or antibodies (intact molecule or Fab fragments) can be coupled covalently to microparticles which have been coated with polysaccharides (such as dextran), using known chemical modifications. This approach has been used commonly in the practice of cell sorting and cell-separation. Molday, et al., 52 *J. Immunol. Methods* 353 (1982) and in the patent herein incorporated by reference.

Moreover, nucleic acids can form complexes with dextran-coated magnetic microparticles which have been modified and coupled with positively-charged biopolymers (ie. poly-L-lysine). A tertiary complex of nucleic acids, proteins (including antibodies) and magnetic microparticles can be formed using information known in the art. It is desirable, but not essential, to keep complexes for use in the present invention less than a micron in size, with superparamagnetic properties intact after modification.

The Cell Preparation & Tissue Types

The present invention may be used with any type of cell preparation, including cells affixed or adhered to a surface, cells suspended in solution, tissue explants and tissues in situ. Primary cells and established cell lines, germ-line as well as somatic cells are amenable to the present methods.

Human adenocarcinoma A549 cells, cervical carcinoma HeLa cells and some non-adherant human primary cord blood cells, human small cell lung cancer cells (H345, SHP77), non-small cell lung cancer cells (H460), human monocytic leukemia cell line U937, M12 and peripheral blood mononuclear cells (PBMC) have been shown useful in the present process. It is important to mention, however, that this process is not limited to these cell lines and can be applied to all other primary or established cell cultures.

However, plant cells and other mammalian cells alike are considered within the scope of the present invention. Bacterial cells are also amenable to the present method. Evidence that biolistic processes results in transfection of cells can be found in Cristou et al., U.S. patent application Ser. No. 5,015,580 (1991) and *Particle Bombardment Technology for Gene Transfer*, (1994) edited by Ning-Sun Yang and Paul Cristou. More recently, several reports have demonstrated particle bombardment utility in transfection of freshly isolated tissue explants samples, including tissue slices, tissue clumps, and cell aggregates, providing a new approach for gene transfer into surgically derived tissue samples. N. S. Yang, 12 *CRC Crit. Rev. Biotechnol.* 335 (1992).

APPLICATIONS OF THE METHOD

Agriculture/Plant Gene Transfer

Economic as well as environmental gains can be made by utilizing the present invention in the agricultural field. Pesticide and fertilizer use may be reduced, crop yields improved, and storage after harvest increased by carefully planning the substances delivered to specific plant cells.

Chapter 3 of Yang and Cristou, cited in the background to the invention, elaborate the possibilities for directed gene transfer in the field of agriculture. Crops which have been transfected using previous particle bombardment technology include: soybean, cotton, papaya, cranberry, tobacco, sunflower and arabidopsis, cucumber, sorghum, rice, wheat, maize, barley, sugarcane, and oat. Tree species have been more difficult to transfect, but poplar has been transfected using previous particle bombardment methods.

The present invention is useful for to transfect any of the above crops and trees, and any plant which is amenable to transfection via particle bombardment is included as within the scope of the present invention. Moreover, the present invention improves on the usefulness of particle bombardment methods because it is less damaging to the cells, and it is safer. Use of the present method in any commercial enterprise, whether for "basic" research or to generate a marketed plant is considered within the scope of the present application.

Therefore, the present invention comprises a method to transfect plants, comprising applying a magnetic force in pulses so as to affect a plurality of magnetic microparticle/nucleic acid complexes, the complexes being in physical proximity to a plurality of plant cells such that when the pulsed high magnetic force is applied, the magnetic microparticles are pulled into the cytoplasm of the cells.

A preferred embodiment of the method to transfect plants is one in which the nucleic acid chosen is DNA. Also preferred is a method to transfect plants, wherein the plant cell type chosen is a cereal grain. A most preferred method to transfect a cereal grain is one wherein the grain is barley.

Also included as within the scope of the present invention is a method to introduce substances other than nucleic acids into plant cells.

Mammalian Gene Transfer and Therapy

The term "gene transfer" is generally used to describe any introduction of nucleic acid into a cell. The cell can be germ line cells, mitochondria, or somatic cells. Researchers often imply, when using this term among themselves, that the goal of the introduction is for molecular biology research, and not particularly for treating a disease state. "Gene therapy," on the other hand, is generally used to describe a particular form of gene transfer, one in which the nucleic acid is introduced to correct or treat a disease state. It is generally accepted that somatic cells only are to be used for gene therapy, and that germ-line cells are not to be used, for ethical reasons.

Lastly "genetic immunization," is generally used to indicate the introduction of a nucleic acid for the purposes of avoiding a disease state, and is therefore somewhat different from the first two terms.

Each of the three terms describe introduction of nucleic acid into a cell. In that respect they are similar. However, in describing the present invention, the generally accepted meaning of "gene transfer," "gene therapy" and "genetic immunization" is intended.

In vitro, ex vivo, and in vivo introduction of nucleic acid into cells via the present methods is within the scope of the present invention. In vitro uses include molecular biology research. Ex vivo transfers of nucleic acids into cells via the present method can be used in gene therapy and genetic immunization, as well as for molecular biology research. Use of the present invention for gene therapy, in vivo, is a preferred embodiment. Other in vivo uses would include genetic immunization and research.

In order to introduce nucleic acid-carrying-magnetic microparticles into mammalian cells in vitro, the cells can be in suspension or adhered to a surface. The cells are then flooded with the magnetic microparticles, and a magnet is pulsed so as to pull the microparticles into the cells. Identification of which cells have been transfected can be of any number of typically acceptable means. For instance, the DNA can be fluorescently or radioactively labeled, and the cells washed after pulsing to remove excess label. The label incorporated into the cells can then be easily identified.

Therefore, the present invention includes a method to introduce nucleic acids into mammalian cells in vitro, comprising applying a magnetic force in pulses so as to affect a plurality of magnetic microparticle/nucleic acid complexes, the complexes being in physical proximity to a plurality of mammalian cells such that when the magnetic force is applied, the magnetic microparticles are pulled into the cytoplasm of the cells.

A preferred embodiment of the method to introduce nucleic acid into mammalian cells in vitro is one in which the nucleic acid chosen is DNA. Preferred methods employ native or linearized plasmids containing an appropriate promoter, reporter genes and DNA of interest as the nucleic acid constructs. Also preferred is a method to introduce nucleic acid into mammalian cells in vitro, wherein the mammalian cell type chosen is a human cell. A most preferred method to transfect a human cell in vitro is one wherein the human cell is an established normal or transformed cell line of a particular tissue of interest.

In order to introduce nucleic acid carrying-magnetic microparticles into mammalian cells ex vivo, cells are removed from the organism, placed in physical proximity to the microparticles, and pulsed with a magnetic force, such that the microparticles are drawn into the cells. The cells can either be studied, or depending on whether the nucleic acid was designed to correct a disease state or immunize, returned to the organism.

Therefore, the present invention comprises a method to introduce nucleic acids into mammalian cells ex vivo, comprising applying a magnetic force in pulses so as to affect a plurality of magnetic microparticle/nucleic acid complexes, the complexes being in physical proximity to a plurality of mammalian cells such that when the magnetic force is applied, the magnetic microparticles are pulled into the cytoplasm of the cells.

A preferred embodiment of the method to introduce nucleic acid into mammalian cells ex vivo is one in which the nucleic acid chosen is DNA. Preferred methods employ native or linearized plasmids containing an appropriate tissue-specific promoter, reporter genes and DNA of interest as the nucleic acid constructs. Also preferred is a method to introduce nucleic acid into mammalian cells ex vivo, wherein the mammalian cell type chosen is a human cell. A most preferred method to transfect a human cell is one wherein the human cell type is brain, mammary gland or peripheral blood lymphocyte.

Promoter-reporter gene vector can be constructed and complexed with poly-lysine conjugated colloidal magnetic microparticles. After magnetic bombardment, gene expression in cell culture at various times can be assessed by measuring the enzymatic activity of the reporter gene. Specific DNA can be constructed with appropriate promoter and reporter gene and delivered into target cells from animals or plants in a similar manner.

In order to introduce nucleic acid into mammals in vivo using the present invention, the magnetic microparticles carrying nucleic acid must be placed in proximity to the tissues within which the nucleic acid is to be introduced. The magnetic force is then applied with the tissue in between the magnet and the microparticles. The tissues can either be studied, or depending on whether the nucleic acid was designed to correct a disease state or immunize, left in the organism.

Therefore, the present invention comprises a method to introduce nucleic acids into mammalian cells in vivo, comprising applying a magnetic force in pulses so as to affect a plurality of magnetic microparticle/nucleic acid complexes, the complexes being in physical proximity to a plurality of mammalian cells such that when the magnetic force is applied, the magnetic microparticles are pulled into the cytoplasm of the cells.

A preferred embodiment of the method to introduce nucleic acid into mammalian cells in vivo is one in which the nucleic acid chosen is DNA. Preferred methods employ native or linearized plasmids containing an appropriate tissue-specific promoter, reporter genes and DNA of interest as the nucleic acid constructs. Also preferred is a method to introduce nucleic acid into mammalian cells in vivo, wherein the mammalian cell type chosen is a human cell. A most preferred method to transfect a human cell is one wherein the human cell type is skin, liver, lung, epidermis, pancreas, dermis, kidney, prostate, ovary, heart and spleen.

Cancer Treatment

The present invention is useful to direct treatment to a solid tumor. With rapidly developing improvements in targeting techniques, including lipid-coating, site-specific ligand or monoclonal antibody conjugation, adenoviral vector conjugation, and selected routes of administration, magnetic microparticles may be targeted and accumulated inside specific regions of an animal or human before exposing to the external pulsed magnet filed. The magnetic pole of the pulse device can be aimed to focus the magnetic field on the internal target of the animal from outside. Thus, delivery of specific systemic gene or magnetic particles carrying chemotherapeutic agents in animals may be achievable.

Therefore, the present invention comprises a method to introduce pharmaceuticals into mammalian cells, comprising applying a magnetic force in pulses so as to affect a plurality of magnetic microparticle/pharmaceutical complexes, the complexes being in physical proximity to a plurality of mammalian cells such that when the magnetic force is applied, the complexes are pulled into the cytoplasm of the cells.

A preferred embodiment of the method to introduce pharmaceuticals into mammalian cells in vivo is one in which the pharmaceutical is chosen from the group consisting of: adriamycin, dexniguldipine, taxol. Preferred methods employ chemotherapeutic drugs carrying charges as the pharmaceutical. Also preferred is a method to introduce pharmaceuticals into mammalian cells in vivo, wherein the mammalian cell type chosen is a human cell.

EXAMPLES

1.) Determination of the magnetic properties of superparamagnetic microparticles When examined under a light microscope, magnetic particles, (superparamagnetic colloidal particles of 40 to 100 nm in diameters), could be seen undergoing Brownian motion in the absence of an applied magnetic field. When an external static magnetic field of moderate strength was applied, the particles became magnetized and formed into chains or needles. These needles were observed for magnetic fields of only a few gauss. Larger fields produced larger needles. After the sudden formation of the needles there were needle-needle interactions causing the needles to coalesce. The needles generally moved past one another parallel to the field until their ends could join. These needles, however, moved slowly toward the applied pole surface. When the magnetic field was removed, the needles broke into segments of a rather spherical shape. These segments diffuse through the liquid so that they are no longer in a chain and finally they are reduced into individual grain of size 40 to 100 nm in diameter again. When a stronger magnetic field of 3000 to 4000 Gauss was applied, such as using a Nd—B—Fe permanent magnet, the same phenomenon could be seen, however, the needles moved much faster toward the applied magnet. The velocity of the moving needles is dependent on the strength of the applied magnetic field.

The magnetic fluid response to a strong magnetic pulse of micro- to millisecond duration and of 4000 to 40.000 gauss of field strength was studied. Due to the design of a pulsed coil and the short pulse duration, it is difficult to use the conventional light microscope to examine the formation of the magnetic needles. To overcome this technical problem, the present inventor designed a new and sensitive capillary magnetic device to monitor the response of magnetic fluid due to a pulsed magnetic field. In this experiment, a capillary tubing was placed inside a test tube consisting of 0.5 ml of magnetic fluid at 30 mg/ml of Fe. The capillary was attached vertically along the side of the test tube with one end of the capillary touching the magnetic fluid. A column of magnetic fluid was drawn up into the capillary due to capillary action. This column of magnetic fluid was very sensitive to the presence of an external magnetic field. Following the movement of an external magnet, this column of magnetic fluid can move up and down the capillary tubing. This response depends on the location, the strength and the quickness of the applied field. This simple "magnetometer" allowed examination of the response of the magnetic fluid to a pulsed field of 2000 to 4000 gauss of 5 μsec to 10 msec pulse duration.

An iron core solenoid of multi-turn coil was constructed and coupled to a capacitor bank. The magnetic fluid "magnetometer" was placed right next to the pole surface of the iron core such that the pole surface is perpendicular to the capillary tubing. The meniscus of the magnetic fluid in the capillary tubing was set right below the pole surface of the iron core. When a pulse of current was sent into the coil, a pulsed magnetic filed was generated and the meniscus of the magnetic fluid responded with a tiny movement. The movement of the meniscus can be followed with an attached view piece. When the amount of pulse current was increased, the strength of the pulsed magnetic field increased correspondingly, as did the movement of the meniscus of the magnetic fluid column in the capillary tubing. The experiments demonstrated that a pulse of 2500 gauss of 10 msec could move the meniscus of the magnetic fluid up the capillary tubing for about 3 to 4 mm. This preliminary experiment clearly showed the feasibility of using a strong pulse field to accelerate superparamagnetic colloidal microparticles.

2.) Penetration of superparamagnetic colloidal microparticles through agarose gel by a strong pulsed magnetic field (commercial magnetizer).

A. A series of petri-dishes (35 mm) consisting of 2 ml of agarose gel of 0.1, 0.2 and 0.3% were prepared and allowed to polymerize.

Thirty ul each of magnetic fluids (20 mg/ml Fe) was diluted into 0.5 ml of distilled water and added onto the polymerized agarose gel. Each dish was then placed inside (but close to the opening of) a commercial 3-inch multi-turn solenoid, where a maximum magnetic gradient could be achieved. The capacitor bank was charged to 700 volts before being discharged into the coil with a silicon-controlled rectifier (SCR). A pulse of 25000 gauss of 10 microseconds was generated by this coil. After each pulse, the dish was taken out and examined for possible penetration of particles into the gel surface. After three continuous pulses, a thin film of particles began to coat the surface of the agarose gel. When six pulses were delivered in the 0.1% agarose gel, many particles of various sizes plus some aggregates appeared at the bottom of the petri-dish. The gel became slightly leaky, such that a layer of diluted magnetic fluid slipped through the gel and appeared at the bottom of the gel. These experiments clearly demonstrated the feasibility of using a strong pulsed field to accelerate magnetic microparticles into a semi-solid matrix support. On one occasion, ferromagnetic particles were able to penetrate 0.1% agarose gel after exposure to only two pulses.

B. A high field and gradient magnet of 24 mm bore, capable of generating up to 50 Teslas with pulse duration of 10 msecond was reserved at the Pulsed Field Facility of the National High Magnetic Field Laboratory Los Alamos National Laboratory for these experiments.

A flat bottom 48 well microtiter plate was obtained from Corning Inc.(25830-48). Individual well was cut from the plate with an electric saw. The dimension of the well is 1 cm in diameter and 1.8 cm in depth. Fresh agarose gel was prepared and layers of gel at 0.2 ml each of 1%, 0.6%, 0.3% , 0.1% were prepared in each well and allowed to polymerize. The thickness of each layer was about 0.21 cm. Several different superparamagnetic and ferromagnetic microparticles were diltued to about 1 mg Fe/ml. 0.1 ml each of these magnetic fluids was pipeted onto the top of the 0.1% agrose gel. The well was then covered with several layers of parafilm to prevent the spill of the magnetic fluid inside the bore of the magnet. This well was inserted inside a specially made sample holder which was then lowered into the bore of the magnet. The well was set at a position of maximum field gradient. The temperaure in the bore area and the sample was maintained at 20° C. A single pulse of 13.6, and 47.3 Teslas was delivered to the sample (S67d, superparamagnetic) but no obvious migration or change of magnetic microparticles was detected. After waiting for about 60 min for the magnet to cool down, another pulse of 46.8 Teslas was delivered to the same sample. A thin layer of magnetic particles could be easily seen at the surface of the 0.1% agarose gel even when the magnetic fluid was removed from the well. The color of the removed fluid was much lighter than the starting material, suggesting some the magnetic microparticles stuck to the surface of the gel after the exposure of the magnetic pulse. When similar magnetic fluid was layered on the 0.1% gel without exposure to magnetic pulse, almost all the liquid could be removed from the gel without leaving any magnetic microparticles behind.

In another experiment, 0.2 ml of ferromagnetic fluid (S21d) at about 1 mg Fe/ml was layered on the top of the 0.1% agarose gel. No obvious migration of the magnetic fluid into the 0.1% gel was detected after exposure to one single pulse of 47.26 Teslas. Since the magnetic particles are ferromagnetic, these particles have some weak magnetic remenence and became magnetized after the exposure to the magnetic pulse. When the same sample was exposed to a second pulse of 47.084 Teslas, about 20% of the magnetic fluid moved into the 0.1% gel layer and stayed at the 0.1–0.3% gel interphase. When another pulse of 47.022 Teslas was delivered to the same sample an hour later, more ferromagnetic microparticles moved through the 0.1% gel layer into the 0.1–0.3% gel interphase. in the same time some the particles at the 0.1–0.3% gel interphase moved into the 0.3% gel layer. This experiment clearly showed that it is possible to accelerate magnetic microparticles into a gel layer, or cells, or tissues under the influence of magnetic pulses.

The experiment was then repeated with another superparamagnetic microparticle type (S87d), which does not have any magnetic memory after exposure to an magnetic field. Two pulses of 47.2 Teslas were delivered to the sample at an interval of one hour, and only a thin layer of magnetic microparticles remained stuck to the surface of the 0.1% gel while most of the magnetic fluid could be removed from the well after the magnetic exposure. This experiment and the above observation clearly demonstrated that the premagnetization of superparamagnetic microparticles is needed in order for the particles to be acted by the second strong magnetic pulse, as opposed to ferromagnetic microparticles which have magnetic memory intact, which will penetrate the first layer when acted upon by one pulse. An ideal primary magnetic field of approximately 200 to 500 gauss is needed to premagnetize the superparamagnetic and/or ferromagnetic microparticles. A second magnetic pulse of at least 2 to 50 Teslas is then immediately applied to the magnetized particles so as to accelerate the particles to a velocity high enough for them to penetrate gel layer, cell membranes or tissues.

3.) Delivery of fluorescently-labeled anti-sense oligomers into human cancer cells by a pulsed magnetic field Human adenocarcinoma cells A549 were plated onto four chamber microscope slides and allowed to attach overnight in a tissue culture incubator. Fluorescently-labeled (FITC) antisense phosphorothioate oligonucleotides of 24 mers of non-specific sequence (#3498) were obtained from Genta, Inc (San Diego) and complexed with cationic lipid-coated superparamagnetic microparticles. The magnetic microparticles were synthesized according to our published procedure without dextran coating. Chan et. al., 122 *J. Mag. & Mag. Mat.* 374 (1993). Cationic lipids 1,2-dimyristyloxypropyl-3-dimethyl-hydroxyethyl ammonium bromide (DMRIE) and DOTAP were obtained from Vical, Inc. or purchased from Avanti Polar Biolipids, and mixed with and equal amount of dioleoyl phosphatidylethanolamine (DOPE). Cationic magneto-liposomes were prepared according to published procedure. A mixture of cationic lipids, DOPE and magnetic particles in organic solvents were mixed, sonicated and dried with a rotary evaporator. The mixture was rehydrated in water and sonicated on ice to generate magneto-liposmes of 100 to 400 nm in size. Fluorescently-labelled oligonucleotides were added to the magneto-liposomes at various DNA/lipid rations in buffered solution. Two ug of DNA/cationic magneto-lipid complexes were added to the A549 cells in each well of the chamber slide.

The chamber slide was then exposed to a pulsed magnetic field by placing an iron-core solenoid coil directly under the slide. After exposing the slide continuously to 30–60 pulses of field strength (4,500 Gauss of 20 msec) the slides were then incubated at 37 degrees celsius for 24 hours. The medium was removed and the slides were washed briefly two times with PBS and examined with a Zeiss Axio-Fluoromicroscope. All of the treated cells had dense fluorescent nuclei, which suggested highly effective delivery of fluorescently-labeled anti-sense oligonucleotides. When compared to the controls, including oligonucleotides alone, oligonucleotide complexed with cationic lipids without magnetic microparticles, and with and without exposing to magnetic pulses, we found that a combination of oligonucleotide/cationic magneto-complexes and a pulsed magnetic field gave the best delivery of fluorescently-labelled DNA into the nuclei of the treated cells.

What is claimed is:

1. A method for delivery of a composition to cells in vitro, said composition comprising a plurality of substance-carrying superparamagnetic microparticles, comprising:

applying a magnetic field in a least two pulses to said composition and cells, wherein said magnetic field is 0.5–50 Teslas in strength, 0.001–200 milliseconds in duration, and insufficient to heat-kill said cells, wherein said magnetic field is applied so as to achieve penetration of the cell membrane by said substance-carrying superparamagnetic microparticles, and said cells are maintainable in viable culture post-delivery.

2. A method of claim 1, wherein the substance is complexed to the superparamagnetic microparticle via a biopolymer coating on the superparamagnetic microparticle.

3. A method of claim 1, wherein the substance is complexed to superparamagnetic microparticle via a lipid coating on the superparamagnetic microparticle.

4. A method of claim 3, wherein the substance is nucleic acid.

5. A method of claim 1, wherein the substance is nucleic acid.

6. A method of claim 1, wherein the cells are mammalian cells.

7. A method of claim 6, wherein the mammalian cells are human cells.

8. A method of claim 7, wherein the human cells are selected from the group consisting of: brain cells; mammary gland cells; peripheral blood lymphocyte cells; skin cells; liver cells; lung cells; pancreatic cells; kidney cells; heart cells; prostate cells; ovary cells and spleen cells.

9. A method of claim 2, wherein the substance is a pharmaceutical compound.

10. A method of claim 9, wherein the cells are human cells.

11. A method of claim 10, wherein the human cells are selected from the group consisting of: brain cells; mammary gland cells; peripheral blood lymphocyte cells; skin cells; liver cells; lung cells; pancreatic cells; kidney cells; heart cells; prostate cells; ovary cells and spleen cells.

12. A method for delivery of a composition to cell in vitro, said composition comprising a plurality of substance-carrying ferromagnetic microparticles, comprising:

applying a magnetic field in a least two pulses to said composition, wherein said magnetic field is 0.5–50 Teslas in strength, 0.001–200 milliseconds in duration, and insufficient to heat-kill said cells, wherein said magnetic field is applied so as to achieve penetration of the cell membrane by said substance-carrying microparticles, and said cells are maintainable in viable culture post-delivery.

13. A method of claim 12, wherein the substance is complexed to the superparamagnetic microparticle via a biopolymer coating on the superparamagnetic microparticle.

14. A method of claim 12, wherein the substance is complexed to the superparamagnetic microparticle via a lipid coating on the superparamagnetic microparticle.

15. A method of claim 14, wherein the substance is a nucleic acid.

16. A method of claim 12, wherein the substance is a nucleic acid.

17. A method of claim 12, wherein the cells are mammalian cells.

18. A method of claim 17, wherein the mammalian cells are human cells.

19. A method of claim 18, wherein the human cells are selected from the group consisting of: brain cells; mammary gland cells; peripheral blood lymphocyte cells; skin cells; liver cells; lung cells; pancreatic cells; kidney cells; heart cells; prostate cells; ovary cells and spleen cells.

20. A method of claim 13, wherein the substance is a pharmaceutical compound.

21. A method of claim 20, wherein the cells are human cells.

22. A method of claim 21, wherein the human cells are selected from the group consisting of: brain cells; mammary gland cells; peripheral blood lymphocyte cells; skin cells; liver cells; lung cells; pancreatic cells; kidney cells; heart cells; prostate cells; ovary cells and spleen cells.

23. A method of claim 1, wherein the cell type transfected is a plant cell.

24. A method of claim 23, wherein the plant cell type transfected is a cereal grain.

25. A method of claim 24, wherein the cereal grain cell type transfected is barley.

26. A method of claim 12, wherein the cell type transfected is a plant cell.

27. A method of claim 26, wherein the plant cell type transfected is a cereal grain.

28. A method of claim 27, wherein the cereal grain cell type transfected is barley.

* * * * *